US008932871B2

(12) United States Patent
Wittkopp et al.

(10) Patent No.: US 8,932,871 B2
(45) Date of Patent: Jan. 13, 2015

(54) OZONE CONVERSION SENSORS FOR AN AUTOMOBILE

(75) Inventors: Scott H. Wittkopp, Ypsilanti, MI (US);
Chang H. Kim, Rochester, MI (US);
Brian T. Heil, Fenton, MI (US)

(73) Assignee: GM Global Technology Operations LLC

( * ) Notice: Subject to any disclaimer, the term of this patent is extended or adjusted under 35 U.S.C. 154(b) by 447 days.

(21) Appl. No.: 13/291,573

(22) Filed: Nov. 8, 2011

(65) Prior Publication Data
US 2013/0034911 A1 Feb. 7, 2013

Related U.S. Application Data

(60) Provisional application No. 61/514,301, filed on Aug. 2, 2011.

(51) Int. Cl.
| | | |
|---|---|---|
| G01N 27/04 | (2006.01) | |
| G01N 27/416 | (2006.01) | |
| G01N 33/00 | (2006.01) | |
| F01N 11/00 | (2006.01) | |
| F01P 3/18 | (2006.01) | |
| F01P 11/12 | (2006.01) | |

(52) U.S. Cl.
CPC . *F01P 3/18* (2013.01); *F01P 11/12* (2013.01); *G01N 33/0039* (2013.01)
USPC ............... 436/135; 60/274; 60/276; 60/277; 73/23.34; 73/31.05; 73/31.06; 73/114.73; 73/114.75; 422/83; 422/90; 422/98; 436/149; 436/151; 436/181

(58) Field of Classification Search
USPC ............ 60/274, 276–277; 73/23.34, 73/31.05–31.06, 114.73, 114.75; 422/83, 422/90, 98; 436/135, 149, 151, 181
See application file for complete search history.

(56) References Cited

U.S. PATENT DOCUMENTS

| | | | | |
|---|---|---|---|---|
| 4,203,946 | A | * | 5/1980 | Ryerson ......................... 422/98 |
| 4,240,798 | A | * | 12/1980 | Wendelin et al. ............. 423/219 |
| 4,243,631 | A | * | 1/1981 | Ryerson ......................... 422/90 |
| 4,294,801 | A | * | 10/1981 | Segawa et al. .................. 422/98 |
| 4,401,967 | A | * | 8/1983 | Miwa et al. ..................... 338/34 |
| 4,885,929 | A | * | 12/1989 | Kasahara et al. ............ 73/31.06 |
| 5,077,970 | A | * | 1/1992 | Hamburg ....................... 60/274 |
| 5,422,331 | A | | 6/1995 | Galligan et al. |
| 5,509,267 | A | * | 4/1996 | Theis .............................. 60/274 |
| 5,533,332 | A | * | 7/1996 | Uchikawa ....................... 60/274 |
| 5,545,377 | A | * | 8/1996 | Fukaya et al. ................ 422/108 |
| 5,546,004 | A | * | 8/1996 | Schmelz ....................... 324/446 |

(Continued)

FOREIGN PATENT DOCUMENTS

JP  2007-64683  3/2007

OTHER PUBLICATIONS

Gengchen Wang, "Atmospheric Ozone Layer and Ozone Hole", 2005, P89, Chapter Three, Beijing, Meteorological Press, (6 pages). (with English translation).

*Primary Examiner* — Arlen Soderquist

(57) ABSTRACT

A system for a vehicle includes a first ozone sensor that generates a first sensor signal indicating a first amount of ozone in air flowing into a radiator. A second ozone sensor generates a second sensor signal indicating a second amount of ozone in air flowing out of the radiator. A control module receives the first sensor signal and the second sensor signal and determines an ozone conversion rate based on the first sensor signal and the second sensor signal.

15 Claims, 3 Drawing Sheets

(56) References Cited

U.S. PATENT DOCUMENTS

| | | | | |
|---|---|---|---|---|
| 5,811,662 A | * | 9/1998 | Williams et al. | 73/31.06 |
| 5,848,527 A | * | 12/1998 | Mitsutani | 60/274 |
| 5,896,743 A | * | 4/1999 | Griffin | 60/274 |
| 6,145,304 A | * | 11/2000 | Takahashi et al. | 60/277 |
| 6,506,605 B1 | | 1/2003 | Allen et al. | |
| 6,543,217 B2 | * | 4/2003 | Alleving et al. | 60/277 |
| 6,660,231 B2 | * | 12/2003 | Moseley | 422/98 |
| 6,797,517 B1 | * | 9/2004 | Hoshi et al. | 436/37 |
| 6,803,236 B2 | * | 10/2004 | Bailey et al. | 436/37 |
| 6,823,727 B2 | * | 11/2004 | Friedel et al. | 73/114.71 |
| 6,835,356 B2 | * | 12/2004 | Okayama et al. | 422/177 |
| 7,038,579 B2 | * | 5/2006 | Hosoe et al. | 340/439 |
| 7,198,952 B2 | * | 4/2007 | Uchida et al. | 436/37 |
| 7,323,343 B2 | * | 1/2008 | Cox et al. | 436/116 |
| 7,926,333 B2 | * | 4/2011 | Odendall | 73/114.75 |
| 2001/0039928 A1 | * | 11/2001 | Alleving et al. | 123/41.49 |
| 2002/0110916 A1 | * | 8/2002 | Fleischer et al. | 436/37 |
| 2003/0066335 A1 | * | 4/2003 | Friedel et al. | 73/23.32 |
| 2003/0093990 A1 | * | 5/2003 | Bayerle et al. | 60/277 |
| 2003/0131650 A1 | | 7/2003 | Bayerle et al. | |
| 2004/0184962 A1 | * | 9/2004 | Klee et al. | 422/83 |
| 2005/0123455 A1 | * | 6/2005 | Inaba et al. | 422/120 |
| 2011/0073285 A1 | | 3/2011 | Benoit et al. | |
| 2011/0121582 A1 | | 5/2011 | Alexander et al. | |
| 2011/0201124 A1 | * | 8/2011 | Schork et al. | 436/135 |
| 2013/0103254 A1 | | 4/2013 | Stewart et al. | |

* cited by examiner

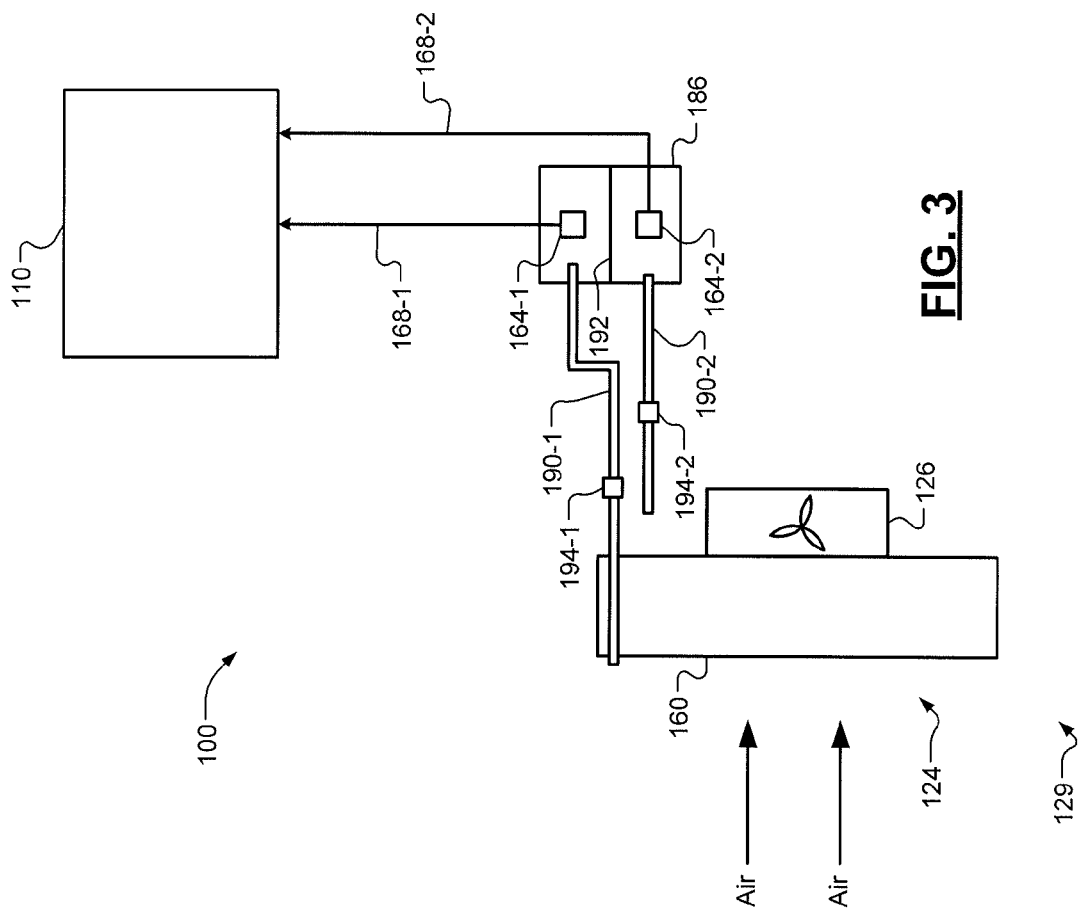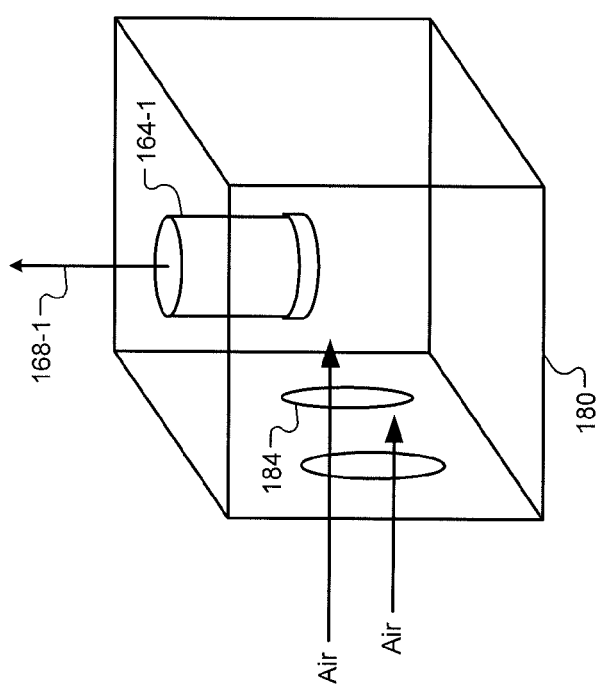

OZONE CONVERSION SENSORS FOR AN AUTOMOBILE

CROSS-REFERENCE TO RELATED APPLICATIONS

This application claims the benefit of U.S. Provisional Application No. 61/514,301, filed on Aug. 2, 2011. The disclosure of the above application is incorporated herein by reference in its entirety.

FIELD

The present application relates to conversion of ozone in vehicle cooling systems.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Combustion of an air/fuel mixture within an internal combustion engine of a vehicle generates heat. Cooling the engine is a cyclical process. Cool engine coolant absorbs heat from the engine, and the (warmed) engine coolant is circulated to a radiator. The radiator facilitates heat transfer from the engine coolant to air passing the radiator. The (cooled) engine coolant is circulated from the radiator back to the engine to absorb more heat from and cool the engine.

A cooling fan may also be implemented to provide airflow past the radiator at times when little air may otherwise pass the radiator. For example only, the cooling fan may be activated to provide airflow past the radiator when a vehicle speed is low or when an aerodynamic shutter is open and airflow past the radiator is low.

The radiator or another heat exchanging structure may implement one or more features to reduce an amount of ground-level ozone in the air flowing into an engine compartment of the vehicle. For example, at least a portion of a surface of the radiator may be coated in a catalyst that converts the ozone in the air into oxygen (e.g., that converts two molecules of O3 into three molecules of O2). For example only, the catalyst may include a PremAir coating.

SUMMARY

A system for a vehicle includes a first ozone sensor that generates a first sensor signal indicating a first amount of ozone in air flowing into a radiator. A second ozone sensor generates a second sensor signal indicating a second amount of ozone in air flowing out of the radiator. A control module receives the first sensor signal and the second sensor signal and determines an ozone conversion rate based on the first sensor signal and the second sensor signal.

A method includes generating a first sensor signal indicating a first amount of ozone in air flowing into a radiator using a first ozone sensor, generating a second sensor signal indicating a second amount of ozone in air flowing out of the radiator using a second ozone sensor, receiving the first sensor signal and the second sensor signal, and determining an ozone conversion rate based on the first sensor signal and the second sensor signal.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 2 illustrates a grounded metal housing for an ozone sensor according to the present disclosure;

FIG. 3 is a functional block diagram of another exemplary vehicle system implementing ozone sensors according to the present disclosure.

DETAILED DESCRIPTION

Figure 1:
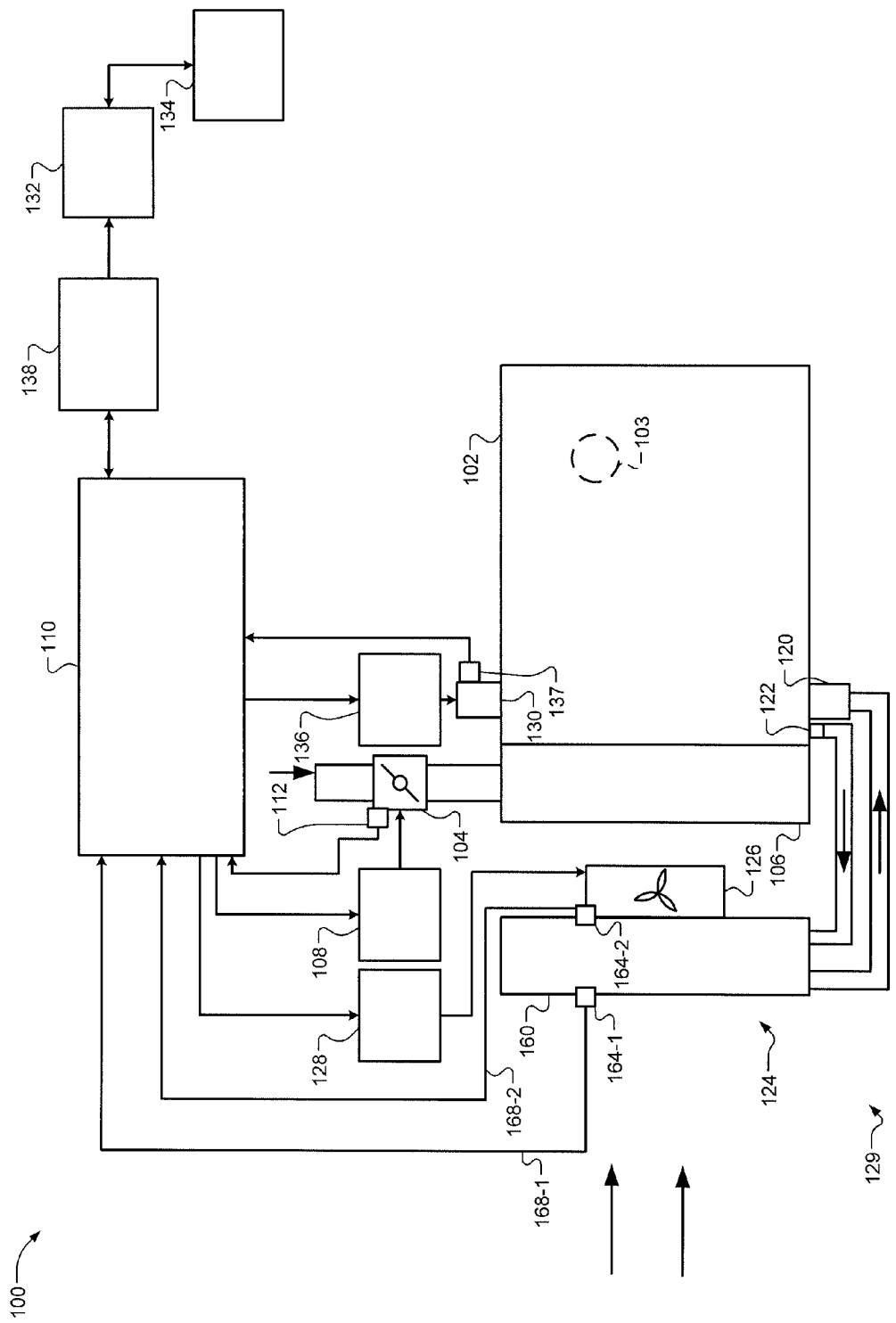
FIG. 1 is a functional block diagram of an exemplary vehicle system implementing ozone sensors according to the present disclosure.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors or a group of execution engines. For example, multiple cores and/or multiple threads of a processor may be considered to be execution engines. In various implementations, execution engines may be grouped across a processor, across multiple processors, and across processors in multiple locations, such as multiple servers in a parallel processing arrangement. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

A vehicle system of the present disclosure includes a radiator or other heat exchanger that implements a catalyst for converting ozone to oxygen. The ability of the catalyst to convert the ozone may decrease over time. For example only, airborne particulate matter may mask the surface of the catalyst over time, preventing air from contacting the catalyst. The vehicle system includes at least first and second ozone sensors. The first ozone sensor senses ozone in the air flowing into an engine compartment of a vehicle prior to passing the radiator. The second ozone sensor senses ozone in the air flowing into the engine compartment after passing the radiator, Accordingly, the measurements of the first and second ozone sensors are indicative of an amount of ozone converted by the radiator (e.g., an ozone conversion rate), and the vehicle system is able to monitor the ability of the catalyst to convert the ozone.

Referring now to FIG. 1, a functional block diagram of an exemplary vehicle system 100 is presented. An engine 102 combusts an air/fuel mixture within one or more cylinders to produce torque for a vehicle. While only cylinder 103 is shown, the engine 102 may include more than one cylinder. Air is drawn into the engine 102 through a throttle valve 104 and an intake manifold 106.

A throttle actuator module 108 controls opening of the throttle valve 104 based on signals from a control module 110. A throttle position (TP) sensor 112 measures a TP (e.g., opening percentage) and generates a TP signal based on the position. Torque produced by the engine 102 may be output via a crankshaft (not shown).

The combustion of the air/fuel mixture generates heat. A coolant may be used to selectively draw heat away from and cool the engine 102. A coolant pump 120 circulates the coolant. When a thermostat 122 is in a closed state, the coolant pump 120 circulates the coolant through coolant channels (not shown) within the engine 102. When the thermostat 122 is in an open state, coolant within the engine 102 is circulated to a radiator 124, and coolant within the radiator 124 is circulated to the engine 102. The thermostat 122 may open when a temperature of the coolant is greater than a predetermined opening temperature. For example only, the predetermined opening temperature may be approximately 85-95° C.

The radiator 124 facilitates heat transfer from the coolant to air passing the radiator 124. In this manner, the radiator 124 facilitates cooling of the coolant. One or more fans, such as fan 126, may push or draw air across the radiator 124 to increase the airflow passing the radiator 124. For example only, the fan 126 may be activated (i.e. turned ON) to increase the airflow passing the radiator 124 when little air would pass the radiator 124, such as when the vehicle is stopped or at a low vehicle speed.

A fan actuator module 128 may control the fan 126 (e.g., ON or OFF) based on signals from the control module 110. For example only, the control module 110 may activate the fan 126 when the coolant temperature is greater than a predetermined fan on temperature. The predetermined fan on temperature may be greater than the predetermined opening temperature and may be, for example, approximately 105° C. In various implementations, the fan 126 may include a variable speed fan.

When more than one fan is implemented, the control module 110 may activate the fans at different predetermined fan on temperatures. For example only, when two fans are implemented, the control module 110 may activate one of the fans when the coolant temperature is greater than the predetermined fan on temperature and activate the other of the fans when the coolant temperature is greater than a second predetermined fan on temperature. The second predetermined fan on temperature may be greater than the predetermined fan on temperature and may be, for example, approximately 113° C.

The fan 126 may also be used to increase airflow within an engine compartment 129 in which the engine 102 is located. Increasing the airflow within the engine compartment 129 may cool components other than the engine 102, the engine coolant, and the radiator 124 that are located within the engine compartment 129. For example only, other components that may be implemented within the engine compartment 129 that may be cooled by the fan 126 may include an air conditioning (AC) unit 130, a motor generator 132, an energy storage device (ESD) 134, and other components implemented within the engine compartment 129. While the fan actuator module 128 is shown and described as being controlled by the control module 110, the fan actuator module 128 may control the fan 126 based on signals from another control module (not shown), such as a chassis control module, a body control module, a hybrid control module, or another suitable module.

An AC control module 136 may control the AC unit 130 based on signals from the control module 110. A compressor (not shown) of the AC unit 130 selectively compresses a refrigerant, and the compressor may be driven by the crankshaft. The AC unit 130 may provide cooling for a passenger cabin of the vehicle. An AC pressure sensor 137 measures pressure of the refrigerant and generates an AC pressure signal based on the pressure. While the AC control module 136 is shown and described as being controlled by the control module 110, the AC control module 136 may control the fan AC unit 130 based on signals from another control module (not shown), such as a chassis control module, a body control module, a hybrid control module, or another suitable module.

The motor generator 132 may provide one or more functions for the vehicle. For example only, the motor generator 132 may supplement the torque output of the engine 102 in some circumstances. The motor generator 132 may apply a braking torque to the engine 102 in some circumstances, such as during regenerative braking. Electrical energy generated by the motor generator 132 during regenerative braking may be stored in the ESD 134 and/or may be supplied to one or more vehicle systems for use. In some implementations, the motor generator 132 may also function as a starter of the engine 102 to crank the engine 102 when the engine 102 is not running. In such implementations, the motor generator 132 may be referred to as a belt alternator starter (BAS). While only the motor generator 132 is shown, the vehicle may include more than one motor generator 132 and more than one motor generator or other electric motor may be included. A hybrid control module 138 may control the motor generator 132 based on signals from the control module 110.

Surfaces of the radiator 124 are coated in a catalyst 160 that converts ozone to oxygen. More specifically, air flowing into the radiator 124 from outside the vehicle system 100 includes ozone. As the air flows through the radiator 124 and over the catalyst 160, the catalyst 160 converts the ozone into oxygen. Accordingly, air flowing into the engine compartment 129 after being treated by the catalyst 160 comprises less ozone than the air flowing into the radiator 124.

The vehicle system 100 includes ozone sensors 164-1 and 164-2. The ozone sensor 164-1 may be located upstream of the radiator 124 and senses an amount of the ozone in the air flowing into the radiator 124 and provides a sensor signal 168-1 accordingly. Conversely, the ozone sensor 164-2 may be located downstream of the radiator 124 senses an amount of the ozone in the air flowing out of the radiator 124 and provides a sensor signal 168-2. The control module 110 receives the sensor signals 168 and determines how much the catalyst 160 is reducing the amount of ozone in the air based on the sensor signals 168. For example only, the control module 110 determines an ozone conversion rate of the catalyst 160 based on a difference between the amount of ozone in the air flowing into the radiator 124 and the amount of ozone in the air flowing out of the radiator 124.

Accordingly, the control module 110 may diagnose one or more of the catalyst 160, the sensors 164 (and/or air flow in the vicinity of the sensors), and communication between the sensors 164 and the control module 110. For example, the control module 110 may compare the ozone conversion rate with a threshold. If the ozone conversion rate is greater than or equal to the threshold, the control module 110 determines that the catalyst 160 is sufficiently converting ozone to oxygen. Conversely, if the ozone conversion rate is less than the threshold, the control module 110 determines that the catalyst 160 is not sufficiently converting ozone to oxygen, or that one or other components (such as one of the sensors 164) is not functioning properly. Accordingly, the control module 110 may take one or more remedial actions such as performing additional diagnoses and/or activating an indicator (e.g., a check engine light) that the vehicle should be serviced. The control module 110 may also adjust determination of the ozone conversion rate based on other known measured or estimated conditions, including, but not limited to, ambient and vehicle temperatures, humidity, vehicle speed, and operation of the fan 126.

For example only, the sensors 164 may include a heated metal oxide semiconductor (HMOS) sensor, an electrochemical sensor, and/or another sensor suitable for detecting ozone (e.g., a UV absorption sensor). The sensors 164 may be sensitive to environmental conditions within the engine compartment 129 that may interfere with the ability of the sensors 164 to sense the ozone in the air. For example, the sensors 164 may be sensitive to temperature, humidity, other chemicals such as hydrocarbons, and/or environmental signals (e.g., EMF and RF signals). Accordingly, the sensors 164 may include one or more structural modifications to prevent the environmental conditions from interfering with the sensors 164.

For example, as shown in FIG. 2, each of the sensors 164 may be encased in a grounded metal housing 180. For example only, the housing 180 is grounded via mechanical communication with the radiator or other suitable structure within the vehicle system 100. The housing 180 shields the sensors 164 from high temperatures and EMF/RF signals while allowing air to reach the sensors 164. For example, the housing 180 may include one or more openings 184 that allow air to reach the sensors 164. Further, the sensors 164 may be at least partially coated in a protective sealant (for example only, an epoxy sealant) to prevent moisture and humidity from damaging or affecting the performance of the sensors 164.

Referring now to FIG. 3, the sensors 164 may also be remotely located from the radiator 124. For example, the sensors 164 may be located in a housing 186 in a passenger compartment, trunk, or other location outside of the engine compartment 129. Accordingly, the vehicle system 100 includes one or more conduits 190 for providing air to the sensors 164. For example, a conduit 190-1 has a first end located upstream of the radiator 124 and a second end located within the housing 186. Accordingly, the conduit 190-1 provides air flowing into the radiator 124 (and into the first end of the conduit 190-1) to the sensor 164-1 via the second end of the conduit. Conversely, a conduit 190-2 has a first end located downstream of the radiator 124 and a second end located within the housing 186. Accordingly, the conduit 190-2 provides air flowing out of the radiator 124 (and into the first end of the conduit 190-2) to the sensor 164-2 via the second end of the conduit 190-2. The sensors 164 may be separated by a partition 192 within the housing 186 to prevent cross contamination of the air provided to the sensors 164.

In this manner, the sensors 164 may provide the signals 168 indicative of the ozone conversion rate of the catalyst 160 while reducing exposure of the sensors 164 to high temperature and other conditions of the engine compartment 129. For example only, one or both of the conduits 190 may include inline fans or air pumps 194-1 and 194-2 that facilitate air flow to the sensors 164. In another implementation, only the conduit 190-1 includes the air pump 194 and the fan 126 is used to facilitate air flow to the sensor 164-2.

Figure 4:
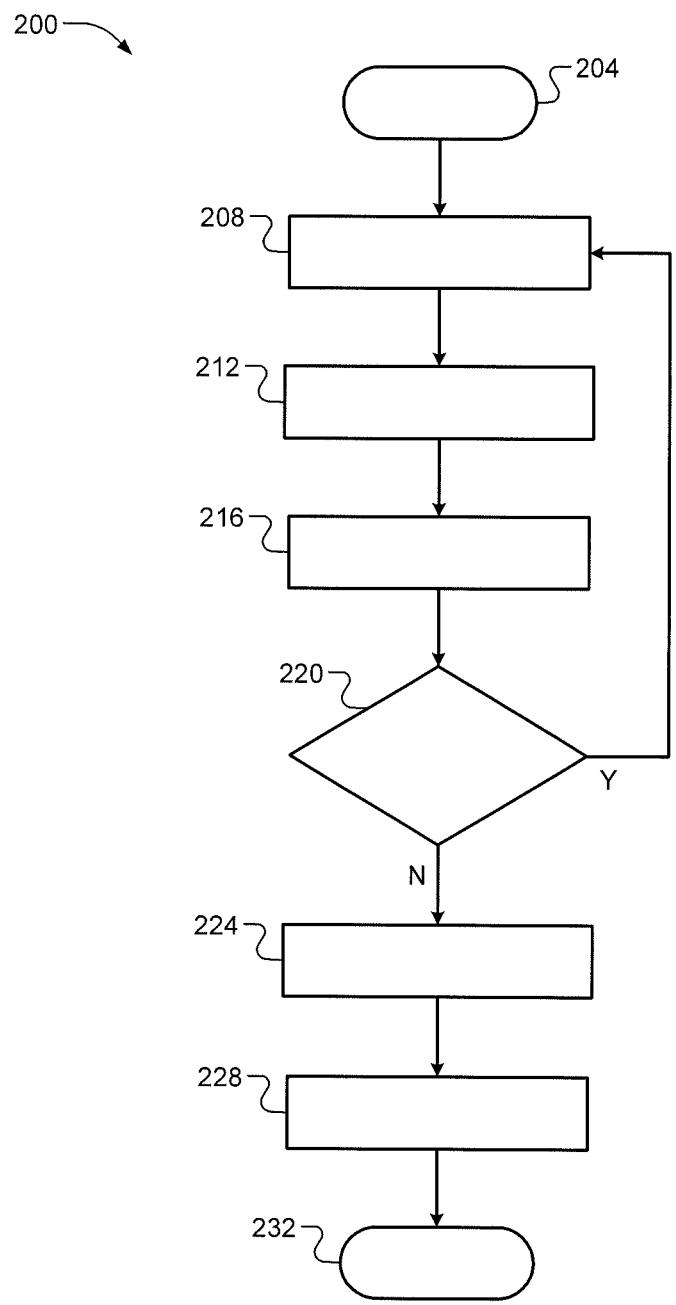
FIG. 4 illustrates an ozone conversion sensing method according to the present disclosure.

Referring now to FIG. 4, an ozone conversion sensing method 200 begins at 204. At 208, the method 200 senses ozone in air flowing into the radiator 124. At 212, the method 200 senses ozone in air flowing out of the radiator 128. At 216, the method 200 determines an ozone conversion rate of the catalyst 160 based on the sensed ozone. At 220, the method 200 determines whether the ozone conversion rate is greater than or equal to a threshold. If true, the method 200 returns to 208 and continues to sense the ozone in the air. If false, the method 200 determines that the catalyst 160 is not sufficiently converting the ozone into oxygen, or that one or more other components related to ozone sensing is faulty at 224. The method 200 activates a fault indicator or takes other remedial action at 228. The method 200 ends at 232.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A system for a vehicle, the vehicle comprising:
 a first ozone sensor that generates a first sensor signal indicating a first amount of ozone in air flowing into a radiator;
 a second ozone sensor that generates a second sensor signal indicating a second amount of ozone in air flowing out of the radiator; and
 a grounded metal housing located outside of an engine compartment of the vehicle, wherein the grounded metal housing encases the first ozone sensor and the second ozone sensor, and wherein the first ozone sensor is partitioned from the second ozone sensor within the grounded metal housing;
 a first conduit having an inlet located upstream from the radiator, wherein the first conduit provides air from the inlet located upstream from the radiator to the first ozone sensor through a first opening in the grounded metal housing;
 a second conduit having an inlet located downstream from the radiator, wherein the second conduit provides air from the inlet located downstream from the radiator to the second ozone sensor through a second opening in the grounded metal housing; and
 a control module that receives the first sensor signal and the second sensor signal and that determines an ozone conversion rate based on the first sensor signal and the second sensor signal.

2. The system of claim 1 wherein a surface of the radiator is coated in a catalyst that converts ozone to oxygen, and wherein the ozone conversion rate corresponds to an ozone conversion rate of the catalyst.

3. The system of claim 2 wherein the control module diagnoses an ability of the catalyst to convert ozone to oxygen based on the ozone conversion rate.

4. The system of claim 1 wherein the control module determines whether the first ozone sensor and the second ozone sensor are functioning properly based on the ozone conversion rate.

5. The system of claim 1 wherein at least one of the first ozone sensor and the second ozone sensor is a heated metal oxide semiconductor (HMOS) sensor.

6. The system of claim 1 wherein at least one of the first ozone sensor and the second ozone sensor is an electrochemical sensor.

7. The system of claim 1 wherein at least one of the first ozone sensor and the second ozone sensor is at least partially coated in a sealant within the grounded metal housing.

8. The system of claim 1 wherein at least one of the first conduit and the second conduit communicates with at least one of a fan and a pump.

9. A method comprising:
   encasing a first ozone sensor and a second ozone sensor in a grounded metal housing located on the outside of an engine compartment, wherein the first ozone sensor is partitioned from the second ozone sensor within the grounded metal housing;
   generating a first sensor signal indicating a first amount of ozone in air flowing into a radiator using the first ozone sensor, wherein a first conduit provides air from an inlet located upstream from the radiator to the first ozone sensor through a first opening in the grounded metal housing;
   generating a second sensor signal indicating a second amount of ozone in air flowing out of the radiator using the second ozone sensor, wherein a second conduit provides air from an inlet located downstream from the radiator to the second ozone sensor through a second opening in the grounded metal housing;
   receiving the first sensor signal and the second sensor signal; and
   determining an ozone conversion rate based on the first sensor signal and the second sensor signal.

10. The method of claim 9 further comprising coating a surface of the radiator in a catalyst that converts ozone to oxygen, wherein the ozone conversion rate corresponds to an ozone conversion rate of the catalyst.

11. The method of claim 10 further comprising diagnosing an ability of the catalyst to convert ozone to oxygen based on the ozone conversion rate.

12. The method of claim 9 further comprising determining whether of the first ozone sensor and the second ozone sensor are functioning properly based on the ozone conversion rate.

13. The method of claim 9 wherein at least one of the first ozone sensor and the second ozone sensor is a heated metal oxide semiconductor (HMOS) sensor.

14. The method of claim 9 wherein at least one of the first ozone sensor and the second ozone sensor is an electrochemical sensor.

15. The method of claim 9 further comprising at least partially coating at least one of the first ozone sensor and the second ozone sensor in a sealant within the grounded metal housing.

* * * * *